United States Patent [19]

Strickland

[11] Patent Number: 5,165,420
[45] Date of Patent: Nov. 24, 1992

[54] BRONCHOALVEOLAR LAVAGE CATHETER

[75] Inventor: Richard D. Strickland, Sandy, Utah
[73] Assignee: Ballard Medical Products, Draper, Utah
[21] Appl. No.: 631,638
[22] Filed: Dec. 21, 1990
[51] Int. Cl.$^5$ .............................................. A61B 5/00
[52] U.S. Cl. .................................... 128/768; 604/19; 604/28; 604/284
[58] Field of Search ............... 128/749, 750, 760, 768, 128/10, 11; 606/106; 604/19, 27, 28, 35, 36, 38, 48, 49, 54, 93, 95, 96, 158, 167, 171, 181, 187, 239, 236-238, 264, 280, 283, 284, 902

[56] References Cited

U.S. PATENT DOCUMENTS

| | | | |
|---|---|---|---|
| 2,786,469 | 3/1957 | Cohen | 128/351 |
| 2,991,787 | 7/1961 | Shelden et al. | 128/351 |
| 3,039,469 | 6/1962 | Fountain | 128/351 |
| 3,225,767 | 12/1985 | Smith et al. | 128/351 |
| 3,319,622 | 5/1967 | Shiner | 128/768 |
| 3,788,305 | 1/1974 | Schreiber | 128/768 |
| 3,948,273 | 4/1976 | Sanders | 128/351 |
| 4,033,353 | 7/1977 | La Rosa | 128/351 |
| 4,037,605 | 7/1977 | Firth | 128/351 |
| 4,072,146 | 2/1978 | Howes | 604/158 |
| 4,235,229 | 11/1980 | Ranford et al. | 128/207.17 |
| 4,239,042 | 12/1980 | Asai | 128/214.4 |
| 4,344,436 | 8/1982 | Kubota | 604/284 |
| 4,351,328 | 9/1982 | Bodai | 128/202.16 |
| 4,416,273 | 11/1983 | Grimes | 128/207.16 |
| 4,434,963 | 3/1984 | Russell | 251/7 |
| 4,525,156 | 6/1985 | Benusa et al. | 604/28 |
| 4,586,691 | 5/1986 | Kozlow | 251/7 |
| 4,622,968 | 11/1986 | Persson | 128/305.3 |
| 4,627,433 | 12/1986 | Lieberman | 128/207.16 |
| 4,637,389 | 1/1987 | Heyden | 604/35 |
| 4,641,646 | 10/1987 | Schultz et al. | 128/207.14 |
| 4,649,913 | 3/1987 | Watson | 128/207.14 |
| 4,669,463 | 6/1987 | McConnell | 128/207.14 |
| 4,683,879 | 8/1987 | Williams | 128/200.26 |
| 4,716,901 | 1/1988 | Jackson et al. | 128/343 |
| 4,838,255 | 6/1989 | Lambert | 128/202.16 |

(List continued on next page.)

FOREIGN PATENT DOCUMENTS

WO89/02761 4/1989 PCT Int'l Appl. .

OTHER PUBLICATIONS

Caughley, et al., "Non–Bronchoscopic Bronchio Alveoli Lavage for the Diagnosis of Pneumocystitis Carinii Pneumonia in the Acquired Immune Deficiency Snydrome", 88 Chest 659–62 (Nov. 1985).

(List continued on next page.)

Primary Examiner—Max Hindenburg
Attorney, Agent, or Firm—Workman, Nydegger & Jensen

[57] ABSTRACT

An outer catheter extending from a point below the first bifurcation of the trachea through the upper respiratory system of the patient is disposed about an inner catheter having a tip secured in the opening at the distal end thereof with an outer lateral periphery larger in diameter than the outer surface of the inner catheter. The proximal surface of the tip between the outer lateral periphery and the outer surface of the inner catheter is capable of sealingly engaging the distal end of the outer catheter. In this condition the pair of catheters can be advanced through the upper respiratory system of the patient without contaminating the outer surface of the inner catheter. Thereafter the inner catheter is advanced relative to the outer catheter into a wedging position in a bronchiole of the patient so as to allow alternative infusing and aspirating a fluid to the bronchiole. The outer catheter, which departs from the longitudinal axis thereof at a predetermined bend angle, possesses sufficient structural rigidity as to be capable, when disposed in the upper respiratory system of the patient of exhibiting at the distal end thereof a one-to-one rotation about the longitudinal axis thereof. Rotation of the proximal end of the outer catheter, accordingly, can direct the bend angle at the distal end toward a preselected branch of the trachea.

61 Claims, 9 Drawing Sheets

U.S. PATENT DOCUMENTS

| | | | |
|---|---|---|---|
| 4,846,191 | 7/1989 | Brockway et al. | 128/748 |
| 4,869,718 | 9/1989 | Brader | 604/164 |
| 4,886,496 | 12/1989 | Conoscenti et al. | 604/96 |
| 4,898,163 | 2/1990 | George | 128/200.26 |
| 4,953,547 | 9/1990 | Poole, Jr. | 128/203.12 |
| 4,981,466 | 1/1991 | Lumbert | 604/19 |
| 4,981,470 | 1/1991 | Bombeck, IV | 128/635 |
| 4,981,477 | 1/1991 | Schon et al. | 604/264 |
| 4,995,384 | 2/1991 | Keeling | 128/207.18 |
| 5,031,613 | 7/1991 | Smith et al. | 128/207.14 |
| 5,054,482 | 10/1991 | Bales | 128/207.14 |
| 5,058,579 | 10/1991 | Terry et al. | 128/207.14 |
| 5,060,645 | 10/1991 | Russell | 128/207.14 |
| 5,060,646 | 10/1991 | Page | 128/207.14 |
| 5,062,420 | 11/1991 | Levine | 128/204.18 |
| 5,067,496 | 11/1991 | Eisele | 128/207.15 |

OTHER PUBLICATIONS

Sobonya, et al., "Detection of Fungi and other Pathogens in Immunocompromised Patients by Bronchio Alveoli Lavage in an Area Endemic for Coccidioidomycosis", 97 Chest 1349-55 (Jun. 1990).

Guerra, et al., "Use of Bronchio Alveoli Lavage to Diagnose Bacterial Pneumonia in Mechanically Ventilated Patients", 18 Critical Care Medicine, 169-73 (Feb. 1990).

Mehta, et al., "The High Price of Bronchoscopy: Maintenance and Repair of the Flexible Fiber Optic Bronchoscope", 98 Chest 448-54 (Aug. 1984).

American Thoracic Society, "Clinical Role of Bronchoalveolar Lavage in Adults with Pulmonary Disease", 142 American Review of Respiratory Disease, 481-486 (Mar. 1990).

Martin, Walter R., et al., "Tracheal Catheters in Patients with Acquired Immunodeficiency Syndrome for the Diagnosis of Pneumocystis Carinii Pneumonia", 96 Chest 29-32 (Jul. 1990).

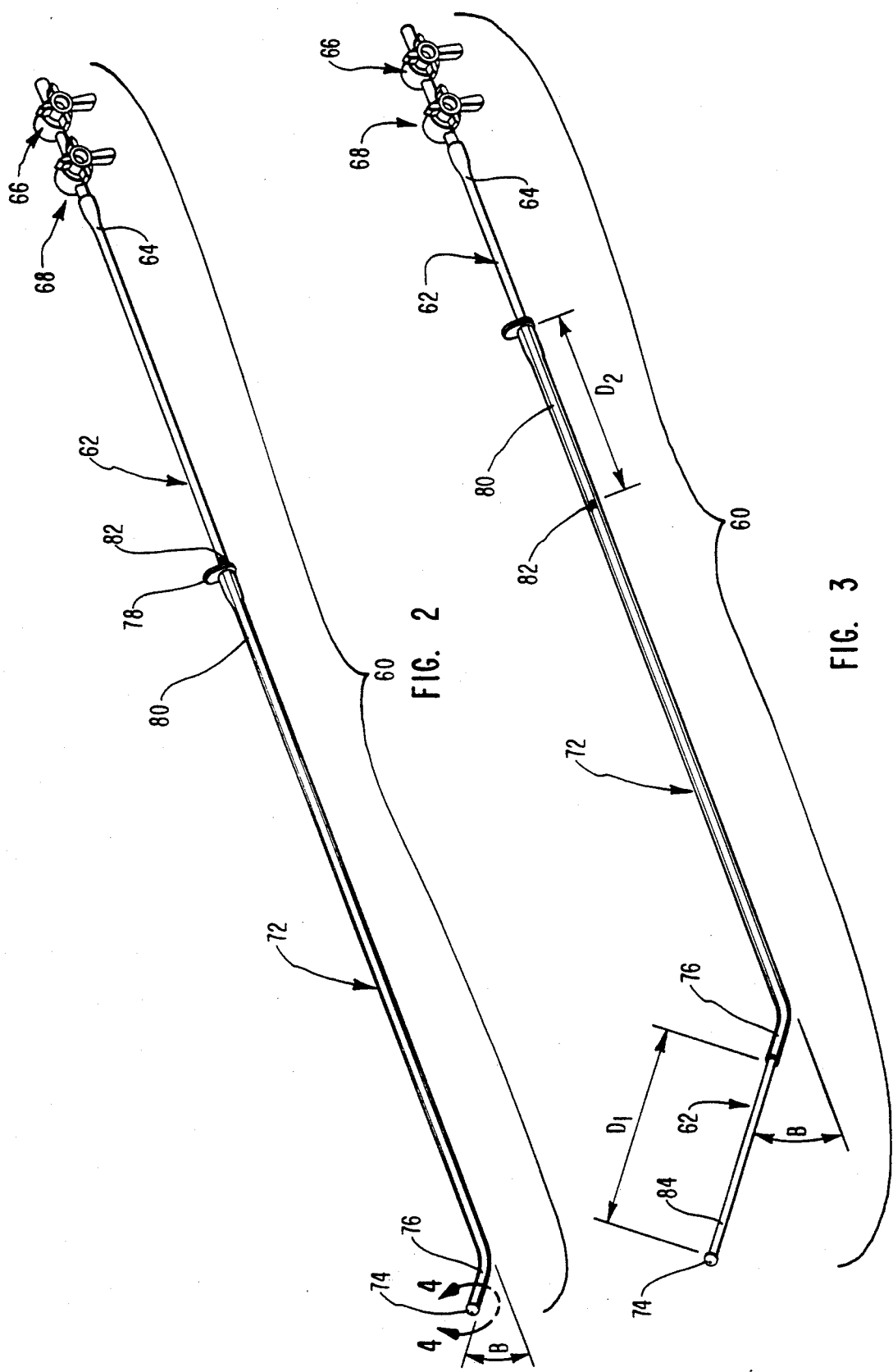

BRONCHOALVEOLAR LAVAGE CATHETER

BACKGROUND

1. Field of the Invention

This invention relates to the diagnosis of abnormal conditions in the lungs, and to a catheter by which to conduct bronchoalveolar lavage. More particularly the present invention relates to a method and apparatus for conducting bronchoalveolar lavage without the use of a bronchoscope.

2. Background Art

The technique of bronchoalveolar lavage has become common in the diagnosis of infections and other abnormalities in the alveoli at the terminus of the bronchiole in the lungs of a patient. In bronchoalveolar lavage, occasionally referred to as "BAL", a sterile fluid is infused in aliquots of about 30 ml. each through the upper respiratory system of a patient into the portion of the lungs thereof designated for study. The fluid infused is then aspirated and cultured and examined in order to isolate and identify infections, fungi, cells, and other signs of inflammation thusly flushed from the walls of the alveoli. Only about 40 to 60% of each infused aliquot can be aspirated. Thus in studies which require large volumes of aspirated fluid, a total infusion of from 30 to about 500 ml. may be required. A helpful background statement on the nature and useful findings related to the use of bronchoalveolar lavage is the American Thoracic Society, "Clinical Role of Bronchoalveolar Lavage in Adults with Pulmonary Disease", 142 AMERICAN REVIEW OF RESPIRATORY DISEASE, 481-486 (1990).

In order to effect the infusion of solution, it has in the past been the practice to utilize a bronchoscope to visually observe the advancement of a catheter through the upper respiratory system of a patient and the branching of the bronchi into a selected bronchiole. During this advancement process, the size of the air passage through which the distal tip of the bronchoscope is advanced gradually decreases until the distal tip of the bronchoscope wedges within the walls of a single bronchiole. This wedge is visually inspected using the bronchoscope, and thereafter the infusion and aspiration of solution is effected through the working lumen of the bronchoscope.

Drawbacks arise, however, in relation to the use of a bronchoscope in this procedure. First, the bronchoscope itself is a very expensive piece of equipment. As a result, it is not practical to dispose of the device following a single use. Instead the bronchoscope must be re-used in order to distribute its expense over a number of procedures. Routine heat based sterilization cannot be used, however. Instead procedures must be employed which are particularly adapted to the delicate nature of the materials comprising the bronchoscope. These sterilization procedures are approximately 24 hours in duration, so that a single costly bronchoscope can be utilized at a given medical establishment only once a day. Thus, a plurality of bronchoscopes must be maintained by a medical establishment if the establishment is to have the opportunity to perform bronchoalveolar lavage more than once a day.

In addition to being extremely delicate in the face of normal sterilization conditions, bronchoscopes are very susceptible to breakage through incorrect use. Like the device itself, repairs on the bronchoscope are extremely expensive. A reference discussing the sources of damage to flexible fiber optic bronchoscopes is Mehta, et al., "The High Price of Bronchoscopy: Maintenance and Repair of the Flexible Fiber Optic Bronchoscope", 98 CHEST 448-54 (August 1984), which is incorporated herein by reference.

Recent literature has forecast a rise in the frequency with which medical practitioners can be expected to resort to the use of bronchoalveolar lavage. The increased incidence of acquired immune deficiency syndrome (AIDS) and other therapeutic-related immunocompromising treatments, such as chemotherapy, gives rise to a large number of patients susceptible to multiple and exotic lung infections. An accurate diagnosis of the identity of these infections is essential, if the patient is to be effectively medicated. Typical of the literature discussing efforts at isolating lung infections in AIDS and other immunocompromised patients are the following:

Caughley, et al., "Non-Bronchoscopic Bronchio Alveoli Lavage for the Diagnosis of *Pneumocystitis carinii* Pneumonia in the Acquired Immune Deficiency Syndrome", 88 CHEST 659-62 (November 1985).

Sobonya, et al., "Detection of Fungi and other Pathogens in Immunocompromised Patients by Bronchio Alveoli Lavage in an Area Endemic for Coccidioidomycosis", 97 CHEST 1349-55 (June 1990).

Guerra, et al., "Use of Bronchio Alveoli Lavage to Diagnose Bacterial Pneumonia in Mechanically Ventilated Patients", 18 CRITICAL CARE MEDICINE 169-73 (1990).

Some difficulties have also been experienced in effecting a clear diagnosis of conditions in the lung due to contamination of the equipment for conducting the bronchoalveolar lavage as the distal end of that equipment is passed through the upper respiratory system of a patient to the lung segment selected for study. In the process of that passage, the exterior of the distal end of the catheter by which infusion and aspiration is actually effected becomes contaminated with micro-organisms in the upper respiratory system of the patient. As a result, the fluid samples aspirated from the lungs thereafter are frequently compromised by cultures of organisms not actually located in the alveoli.

When a bronchoscope is not utilized, problems have been experienced in locating the distal tip of the sampling catheter in a specific preselected lung to be studied, placement in the left lung being particularly difficult due to inherent anatomical structure of the bronchi. Fluoroscopic and X-ray methods for verifying the location of a distal tip can to an extent be useful in assisting and directing the distal tip into a specific preselected lung, but these methods are totally incapable of replacing the primary value of bronchoscope use, namely the verification of distal tip wedging in a bronchi of the patient to the extent required for successful infusion and aspiration of fluid. Fluoroscopic and X-ray methods for effecting placement are also complicated to utilize, and may be limited by availability to large medical institutions.

BRIEF SUMMARY AND OBJECTS OF THE INVENTION

One object of the present invention is to improve the accuracy of diagnostic efforts directed to inflammations and other abnormalities in the lungs.

It is a related object of the present invention to increase the ease and reduce the costs of conducting bronchoalveolar lavage.

Another object of the present invention is to facilitate the use of bronchoalveolar lavage without resort to costly bronchoscopic techniques.

It is another object of the present invention to permit frequent bronchoalveolar lavage sampling.

Yet another object of the present invention is to produce a bronchoalveolar lavage catheter which is adequately inexpensive to produce so as to be disposable.

Another object of the present invention is a disposable bronchoalveolar lavage catheter which does not require the use of a bronchoscope to confirm proper placement of the catheter prior to infusion and aspiration.

Yet another object of the present invention is to provide a bronchoalveolar catheter which is capable of being located in one or the other of the lungs with a high degree of reliability.

Yet another object of the present invention is to prevent contamination of the exterior surface of a catheter by which bronchoalveolar lavage is being conducted during the passage of that catheter through the upper respiratory system of the patient.

It is yet another object of the present invention to produce a bronchoalveolar lavage catheter as described which is useable in patients with or without mechanical ventilation.

It is an object of the present invention to permit bronchoalveolar lavage sampling of lung segments of varying sizes.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein an apparatus and method are provided for conducting bronchoalveolar lavage without the use of bronchoscopy. Accordingly, a catheter is provided comprising an outer catheter and an inner catheter disposable therein. The outer catheter is so sized and configured as to extend from a point below the first bifurcation of the trachea of a patient through the upper respiratory system of the patient. The distal end of the outer catheter departs from the longitudinal axis thereof at a predetermined bend angle. The inner catheter is so sized and configured as to extend from a bronchiole in the lung of the patient through the upper respiratory system of the patient. The distal end of the inner catheter wedges at whatever level of bronchi branching in the lung is appropriate according to the size of the inner catheter. The catheter further comprises means located at the proximal end of the inner catheter for infusing and aspirating fluid through the inner catheter.

Typically the means for infusing and aspirating comprises a sampling stopcock located at the proximal end of the sampling catheter. The sampling stopcock is connectable to a reservoir of a fluid and to a syringe for infusing the fluid through the inner catheter The sampling stopcock is capable of placing the syringe alternately in communication with the reservoir of fluid or with the proximal end of the inner catheter.

According to another aspect of the invention, the inner catheter comprises a first closure means located at the distal end of the inner catheter for sealing the distal end of the outer catheter when the outer catheter is disposed encircling the inner catheter with the distal end of the inner catheter at the distal end of the outer catheter. In the embodiment disclosed herein, the first closure means comprises a tip at the distal end of the inner catheter. The tip has an outer lateral periphery having a diameter greater than the outer surface of the inner catheter. Between the outer lateral periphery of the tip and the outer surface of the inner catheter the tip has a proximal surface which is capable of sealingly engaging the distal end of the outer catheter when the outer catheter is disposed encircling the inner catheter with the distal end of the inner catheter at the distal end of the outer catheter. An aperture is centrally formed through the tip of the inner catheter to communicate with the interior of the inner catheter. Typically the tip is secured in the opening at the distal end of the inner catheter. Optionally, the tip may be comprised of a radiopaque material.

The inner catheter is provided with a position indicator mark at the location on the inner catheter disposed at the proximal end of the outer catheter when the tip of the inner catheter sealingly engages the distal end of the outer catheter.

With the proximal surface of the tip engaging the distal end of the outer catheter, the outer catheter with the inner catheter disposed therein can be advanced through the upper respiratory system of the patient without contaminating the outer surface of the inner catheter. Thereafter, the inner catheter is advanced relative to the outer catheter and any mucous accumulated in the aperture through the tip thereof is flushed out prior to advancement of the tip into a wedging position in a bronchiole of the patient.

In another aspect of the present invention, the inner catheter comprises a second closure means for facilitating and sustaining wedging of the distal end of the catheter into a bronchiole of the patient. In the embodiment of the invention disclosed herein, such a second closure means takes the form of a tip at the distal end of the inner catheter having a lead surface that comprises a smoothly curving dome that terminates at the outer lateral periphery of the tip. Centrally formed in the dome is an aperture therethrough communicating with the interior of the inner catheter. The outer lateral periphery of the tip has a diameter larger than the outer surface of the inner catheter.

The radially symmetric shape of the dome permits the tip to advance into a bronchiole and easily engage the walls thereof about the full lateral periphery. Thereafter, dewedging of the tip from that bronchiole is resisted by the enlarged lateral periphery of the tip relative to the outer surface of the inner catheter. That lateral periphery affords enhanced purchase on the tip by the tissue of the bronchiole wall, much in the manner in which an atraumatic barb resists removal. Nevertheless, the enlarged lateral periphery of the tip is rounded in shape so as to reduce trauma to tissue in the bronchiole wall during the process.

Typically, the inner catheter comprises a single lumen so sized as to permit the infusion and aspiration of a fluid therethrough. Alternatively, however, the inner catheter can comprise a first lumen so sized as to permit such infusion and aspiration, as well as a second lumen having a size relatively smaller than that of the first lumen and being capable of transmitting a gas between the distal and the proximal ends of the inner catheter.

Under such circumstances, the inner catheter further comprises a flexible cuff attached to and encircling the sides of the inner catheter proximal of the distal end thereof. The cuff is selectively inflatable through the second lumen to engage the walls of the bronchiole of the patient. Through the use of such an inflatable cuff, the distal tip of the inner catheter can in effect be wedged in a major bronchia, thereby to permit sampling of a larger lung segment than would be possible, if the distal tip of the catheter were to be advanced into the lung far enough to wedge in a single bronchiole.

In another aspect of the present invention, the outer catheter possesses sufficient structural rigidity as to be capable, when disposed in the upper respiratory system of the patient, of exhibiting at the distal end thereof a one-to-one rotation about the longitudinal axis thereof relative to the proximal end thereof. Correspondingly, the proximal end of the outer catheter is provided with a direction indicator designating the direction at which the bend departs from the longitudinal axis of the inner catheter. Through the use of the position indicator, the bend may be directed toward the desired primary branch of the trachea in order to then advance the outer catheter with the inner catheter disposed therein into a preselected lung of the patient.

Optionally, the catheter disclosed comprises a means for monitoring pressure in the airways of the patient toward the end, for example, of assisting in verifying correct wedging of the distal tip of the inner catheter. Such a means can take the form of a pressure stopcock located between the proximal end of the inner catheter and the means for infusing and aspirating. The pressure stopcock is capable of selectively placing the proximal end of the inner catheter in communication alternatively with the pressure monitor or with the means for infusing and aspirating.

By means of the apparatus and method of the present invention, bronchoalveolar lavage can be performed in an efficient and economical manner using equipment of such low cost as to be disposable. The catheter of the present invention provides the medical practitioner with the capacity to direct the bronchoalveolar lavage catheter toward a preselected one of the lungs of the patient, while protecting the exterior of the catheter which is advanced into the preselected lung from contamination as that catheter is advanced through the upper respiratory system of the patient. In addition, the unique shape of the tip of that sampling catheter facilitates the effecting and maintenance of desired wedging. Alternatively, wedging can be accomplished in larger air passageways using an inflatable cuff located proximal of the distal end of the catheter.

The present invention also contemplates a method for performing non-bronchoscopic bronchoalveolar lavage.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which:

FIG. 2 is a perspective view of the inventive bronchoalveolar lavage catheter with the distal ends of the outer and inner catheter in sealing engagement;

FIG. 3 is a perspective view of the bronchoalveolar lavage catheter shown in FIG. 2 with the distal end of the inner catheter advanced out of the distal end of the outer catheter;

DETAILED DESCRIPTION OF THE PREFERRED EMBODIMENTS

Figure 1:
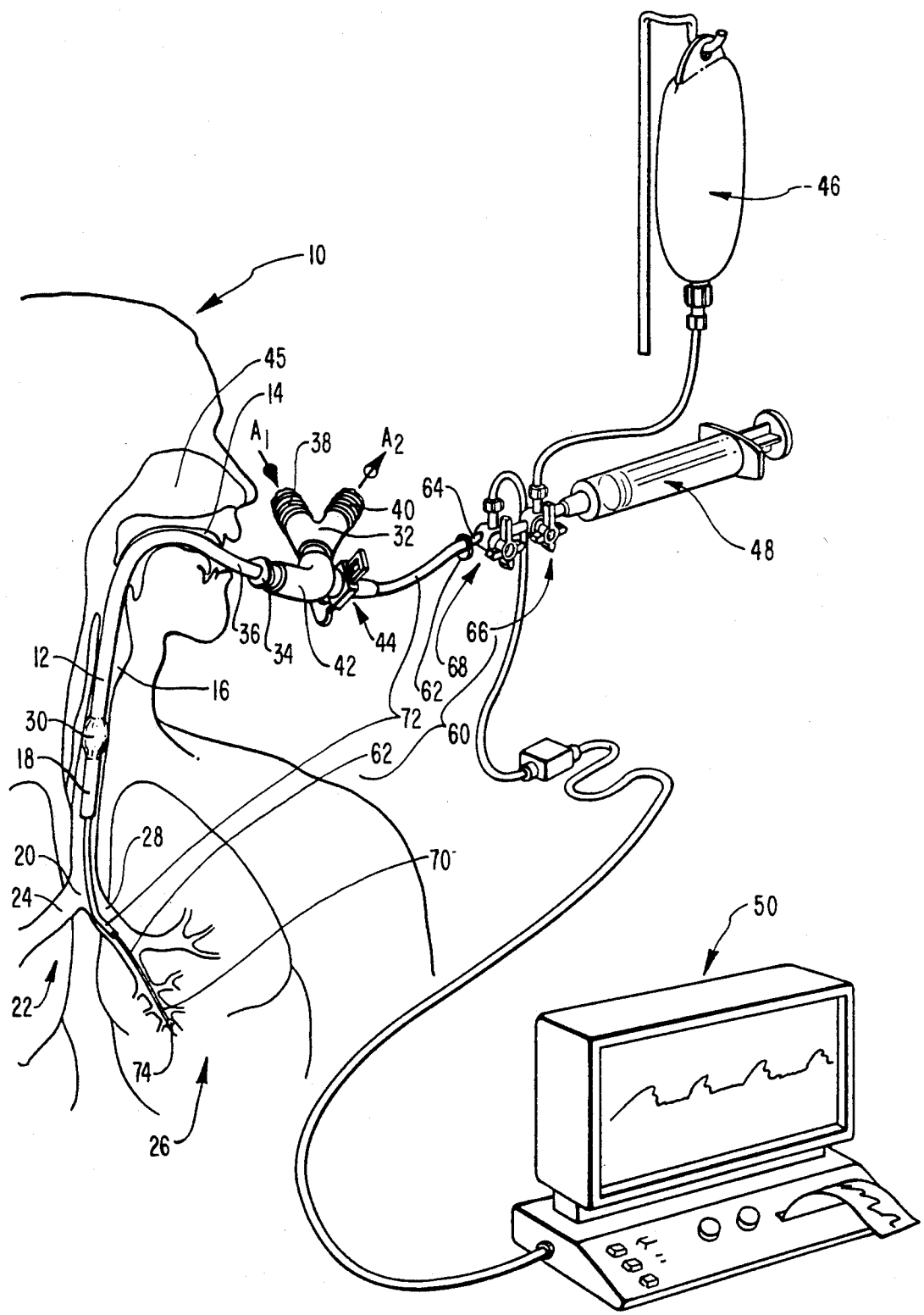
FIG. 1 is a schematic drawing of a system for conducting bronchoalveolar lavage using the inventive bronchoalveolar lavage catheter.

FIG. 1 illustrates the environment in which the inventive bronchoalveolar lavage catheter is employed in relation to a patient 10 intubated with an endotracheal tube 12. Although intubation is not required in order to perform bronchoalveolar lavage with the inventive catheter disclosed herein, intubation may be employed expressly for the purpose of facilitating the procedure of bronchoalveolar lavage. Generally, however, intubation is undertaken in order to provide ongoing mechanical ventilation of a patient.

As seen in FIG. 1, endotracheal tube 12 extends through the mouth 14 and the trachea 16 of the upper respiratory system of patient 10, terminating in a distal end 18 well above the point 20 at the first bifurcation of trachea 16 into the right lung 22 through the right mainstem bronchus 24 and into the left lung 26 through the left mainstem bronchus 28. Typical sub-branchings of the mainstem bronchus are shown in FIG. 1 for illustrative purposes in relation to the sub-branching of left mainstem bronchus 24 into left lung 26.

Distal end 18 of endotracheal tube 12 is provided with a balloon 30 which, when inflated, engages the walls of trachea 16 to facilitate mechanical ventilation of patient 10 through a Y-connector 32 coupled to a standard endotracheal tube adapter 34 at the proximal end 36 of endotracheal tube 12. Air from the ventilating apparatus for patient 10 enters endotracheal tube 12 through a first leg 38 of Y-connector 32, as indicated in FIG. 1 by arrow $A_1$. Correspondingly, air is returned to the ventilating apparatus from patient 10 through a second leg 40 of Y-connector 32, as shown in FIG. 1 by arrow $A_2$.

An elbow coupling 42 connects endotracheal tube adapter 34 with Y-connector 32 and is provided at a point on the outer radius thereof with a bronchoalveolar lavage catheter port 44 through which a bronchoalveolar lavage catheter can be entered into endotracheal tube 12 and advanced therethrough into a preselected lung of patient 10 without losing the positive end expiratory pressure (PEEP) often required during mechanical ventilation.

It must be emphasized that use of the inventive bronchoalveolar lavage catheter disclosed herein is not limited to use with patients undergoing mechanical ventilation, or even patients in whom intubation with an endotracheal tube has occurred. In addition, as will be apparent subsequently, bronchoalveolar lavage can be conducted with the inventive bronchoalveolar lavage catheter through the nasal passages 45 of patient 10, rather than through the mouth 14 thereof.

As illustrated in FIG. 1, bronchoalveolar lavage is to be performed on a portion of left lung 26 of patient 10. In the process, a sterile fluid from a reservoir 46 thereof is infused into individual aliquots using a syringe 48. The fluid of each infusion is then aspirated using either syringe 48 or the wall vacuum (not shown) in the medical institution in which the bronchoalveolar lavage is conducted. Advantageously, the procedure of bronchoalveolar lavage and in particular the proper wedging of the distal tip of the inventive bronchoalveolar lavage catheter into a bronchiole in left lung 26 of patient 10 is facilitated through the monitoring of air passageway pressures at the distal end of the bronchoalveolar lavage catheter. Toward this end, an air passageway monitor 50 is illustrated having either or both a cathode ray tube display or visual printout.

One embodiment of a bronchoalveolar lavage catheter 60 incorporating teachings of the present invention is illustrated in FIG. 1 coupling reservoir 46, syringe 48, and air passageway pressure monitor 50 through endotracheal tube 12 to left lung 26 of patient 10. Bronchoalveolar lavage catheter 60 is an assembly of subcomponents functioning together for the purpose stated. Nevertheless, it will be understood from the disclosure which follows that some or all of the components thereof may be eliminated from bronchoalveolar lavage catheter 60, while yet incorporating some teachings of the present invention. As shown in FIG. 1, bronchoalveolar lavage catheter 60 includes an inner sampling catheter 62 so sized and configured as to extend from a distal bronchiole in left lung 26 of patient 10 through the upper respiratory system to a connection external patient 10.

According to one aspect of the present invention, at proximal end 64 of sampling catheter 62, means are provided for infusing and aspirating fluid through sampling catheter 62 into the lung of a patient. As shown by way of example and not limitation, a sampling stopcock 66 is coupled to proximal end 64 of sampling catheter 62. Sampling catheter 66 is capable of connection to reservoir 46 and to syringe 48 in such a manner as to selectively place syringe 48 alternately in communication with reservoir 46 or with proximal end 64 of sampling catheter 62.

In another aspect of the inventive bronchoalveolar lavage catheter, means are provided for monitoring pressure in the airways of patient 10. As shown by way of example and not limitation, in FIG. 1 a pressure stopcock 68 is located between proximal end 64 of sampling catheter 62 and sampling stopcock 66. Pressure stopcock 68 is capable of selectively placing proximal end 64 of sampling catheter 62 in communication alternately with air passageway pressure monitor 50 or with sampling stopcock 66. In the latter condition, it is impossible to infuse and aspirate fluid from reservoir 46 through sampling catheter 62. When the process of infusion and aspiration is not ongoing, the placement of air passageway pressure monitor 50 in communication with sampling catheter 62 by the appropriate manipulation of pressure stopcock 68 enables a medical practitioner to evaluate the air pressure patterns in the air passageways of patient 10 distal of the tip of distal end 70 of sampling catheter 62, thereby to verify correct wedging of the tip of distal end 70 of sampling catheter 62 in a bronchiole of patient 10.

In yet another aspect of the present invention, bronchoalveolar lavage catheter 60 includes a means for directing distal end 70 of sampling catheter 62 into a preselected lung of patient 10, while also protecting the outside of sampling catheter 62 from contamination during the advancement of distal end 70 of sampling catheter 62 through the upper respiratory system of patient 10. As shown by way of example and not limitation, bronchoalveolar lavage catheter 60 comprises an elongated outer catheter or insertion sheath 72 so sized and configured as to encircle sampling catheter 62 and to be capable of extending from a location below the point 20 at the first bifurcation of trachea 16 through the upper respiratory system of patient 10.

The structure of insertion sheath 72 and interaction thereof with sampling catheter 62 during the process of conducting bronchoalveolar lavage with bronchoalveolar lavage catheter 60 will be more clearly appreciated by reference first to FIG. 2. There sampling catheter 62 is disposed within insertion sheath 72 with the tip 74 of sampling catheter 62 at distal end 76 of insertion sheath 72. The ability of bronchoalveolar lavage catheter 60 to effect bronchoalveolar lavage in a preselected lung of patient 10 is dependent both upon the structure of distal end 76 of insertion sheath 72 and upon the material of which insertion sheath 72 is comprised.

As seen in FIG. 2, distal end 76 of insertion sheath 72 is displaced at a predetermined bend angle B to the longitudinal axis of insertion sheath 72. A direction indicator 78 at proximal end 80 of insertion sheath 72 projects from insertion sheath 72 in the same radial direction as the radial direction at which distal end 76 of insertion sheath 72 departs from the longitudinal axis thereof.

Insertion sheath 72 is comprised of a relatively rigid material, such as ethyl vinyl acetate. In this manner, insertion sheath 72 will by design possess sufficient structural rigidity as to be capable, when disposed in the warm, upper respiratory system of patient 10, of nevertheless exhibiting at distal end 76 one-to-one rotation about the longitudinal axis of insertion sheath 72 relative to proximal end 80 thereof. In this manner, when insertion sheath 72 is disposed in the upper respiratory system of patient 10, as shown in FIG. 1, the rotation of proximal end 80 of insertion sheath 72 about the longitudinal axis thereof will result in an identical rotation of distal end 76 of insertion sheath 72 about the longitudinal axis thereof. Direction indicator 78 outside the body of patient 10 will at all times be oriented in the radial direction at which distal end 76 departs from the longitudinal axis of insertion sheath 72, thereby affording information to a medical practitioner about the direction of distal end 76 of insertion sheath 72 inside the body of patient 10. By utilizing this feature of bronchoalveolar lavage catheter 60, it will be seen subsequently that sampling catheter 62 can be advanced with certainty into a preselected lung of patient 10.

A position indicator mark 82 is provided on sampling catheter 62 at the location thereupon which is disposed at proximal end 80 of insertion sheath 72 when tip 74 of sampling catheter 62 is located at distal end 76 of insertion sheath 72. As will be discussed in further detail subsequently, in this relative position of sampling catheter 62 and insertion sheath 72, tip 74 sealingly engages distal end 76 of insertion sheath 72.

Insertion sheath 72 and sampling catheter 62 are relatively sized so that sampling catheter 62 can slide freely within insertion sheath 72. Thus, as shown in FIG. 3, sampling catheter 62 can be advanced into and through insertion sheath 72, so that tip 74 moves away from distal end 76 of insertion sheath 72 a distance $D_1$ revealing distal end 84 of sampling catheter 62. Correspondingly, position indicator mark 82 is advanced into proximal end 80 of insertion sheath 72 by distance $D_2$ equal to the distance $D_1$ by which distal end 84 of sampling catheter 62 advances out of distal end 76 of insertion sheath 72. The initial direction in which distal end 84 of sampling catheter 62 advances from insertion sheath 72 is determined by the orientation of the bend at distal end 76 of insertion sheath 72.

In use, insertion sheath 72 is disposed in the upper respiratory system of patient 10, and insertion sheath 72 is rotated about the axis thereof to orient direction indicator 78 and distal end 76 of insertion sheath 72 toward a preselected one of lungs 22, 26. Then sampling catheter 62 is advanced out of insertion sheath 72 in the manner illustrated in FIG. 3 Doing so necessarily results in distal end 84 of sampling catheter 62 advancing into the same preselected lung. Thereafter, distal end 84 of sampling catheter 62, which desirably is more pliable than that of insertion sheath 72, is able to advance despite its pliable structure into the preselected lung.

Figure 4:
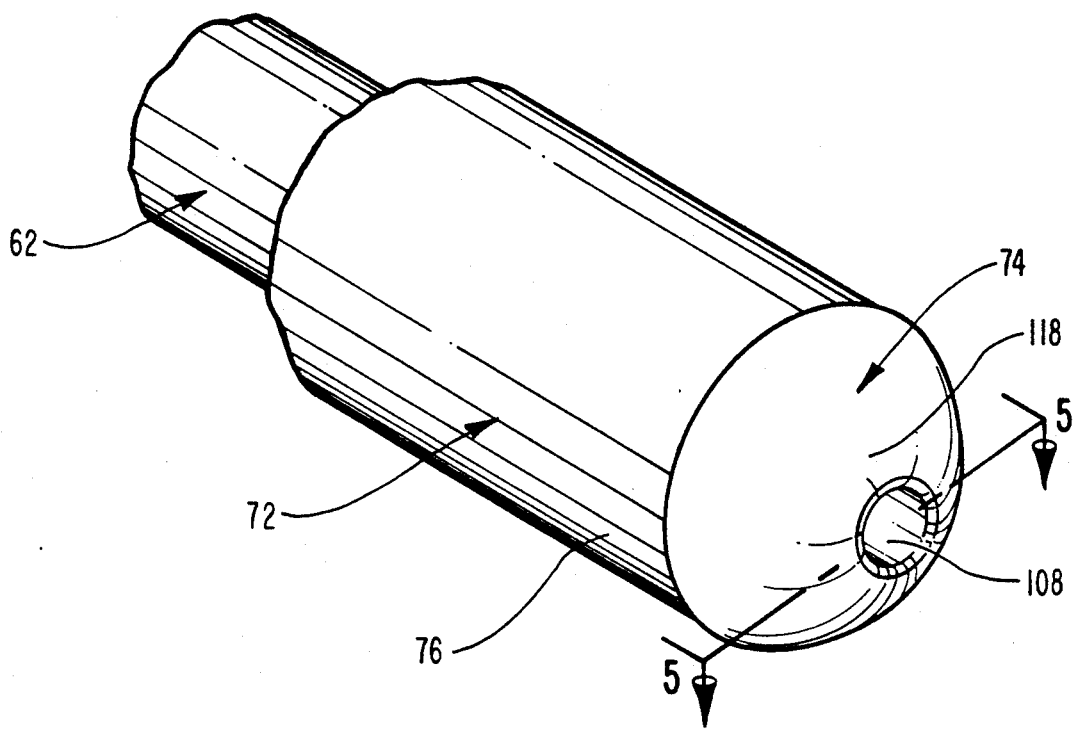
FIG. 4 is a perspective detailed view of the distal ends of the inner and outer catheters and the tip of the inner catheter of the bronchoalveolar lavage catheter shown in FIG. 2.
Figure 5:
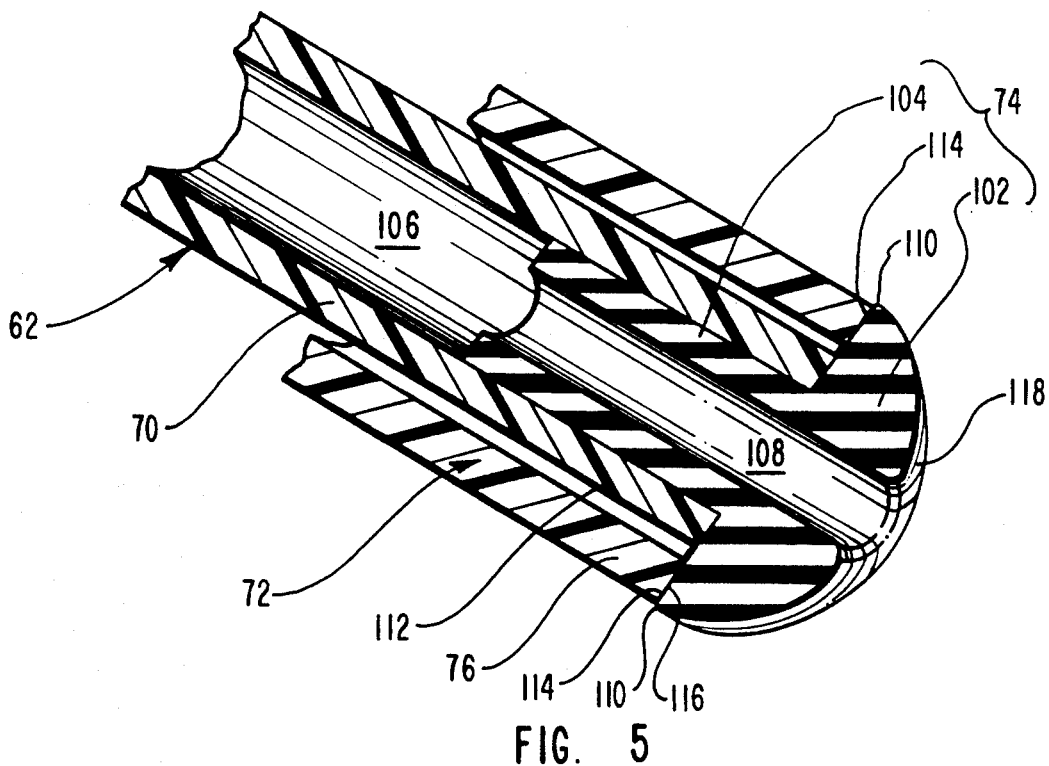
FIG. 5 is a cross-sectional view of the tip of the bronchoalveolar lavage catheter shown in FIG. 4 and taken along section line 5—5 therein.
Figure 6:
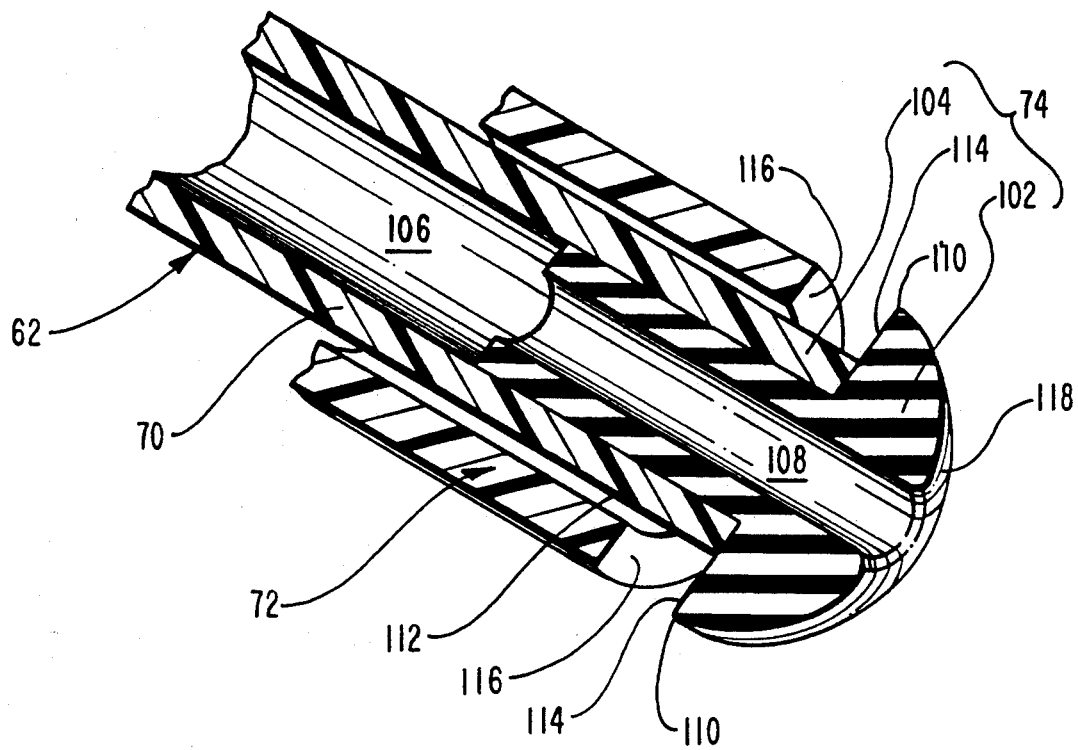
FIG. 6 is a cross-sectional view of the tip of the bronchoalveolar lavage catheter shown in FIG. 4 with the distal end of the inner catheter advanced out of the distal end of the outer catheter.

According to another aspect of the present invention, sampling catheter 62 comprises a first closure means located at distal end 70 thereof for sealing distal end 76 of insertion sheath 72 when insertion sheath 72 is disposed encircling sampling catheter 62 with distal end 70 of sampling catheter 62 at distal end 76 of insertion sheath 72. This is the relative positioning of sampling catheter 62 and insertion sheath 72 shown in FIG. 2 with position indicators mark 82 being located just at the terminus of proximal end 80 of insertion sheath 72. The first closure means associated with inner catheter 62 is best appreciated, by way of example and not limitation, by reference to the detailed view of tip 74 shown in perspective in FIG. 4 and in cross-section in FIGS. 5 and 6. In the cross-section of FIG. 5, tip 74 is shown making sealing engagement with distal end 76 of insertion sheath 72, while in FIG. 6, sampling catheter 62 has been advanced relative to insertion sheath 72 in the manner illustrated in FIG. 3, so as to separate tip 74 from distal end 76 of insertion sheath 72.

Tip 74 comprises a radially symmetrical insert secured in distal end 70 of sampling catheter 62. Tip 74 comprises a head portion 102 and a stem portion 104 which is received within and secured to the bore of the lumen 106 centrally formed in sampling catheter 62. Tip 74 may be comprised of a radiopaque material to render it locatable by x-ray or fluoroscopic examination when inside the body of patient 10.

Centrally formed through tip 74 is an aperture 108 which communicates with lumen 106 at the interior of sampling catheter 62. Head portion 102 of tip 74 has an outer lateral periphery 110 which is larger in diameter than the outer surface 112 of sampling catheter 62. Between outer lateral periphery 110 of tip 74 and outer surface 112 of sampling catheter 62, head portion 102 of tip 74 defines an annular proximal surface 114 which encircles and is normal to outer surface 112 of sampling catheter 62 when tip 74 is secured in distal end 70 of sampling catheter 62.

When insertion sheath 72 and sampling catheter 62 are in the relative positions illustrated in FIG. 2, annular proximal surface 114 of tip 74 engages lateral surface 116 (FIGS. 5 and 6) at the terminus of distal end 76 of insertion sheath 72. Under such conditions, insertion sheath 72 with sampling catheter 62 disposed therein can be advanced through the upper respiratory system of patient 10, while protecting outer surface 112 of sampling catheter 62 from contamination by microorganisms residing the upper respiratory system. Sampling catheter 62 is advanced out of insertion sheath 72, exposing outer surface 112 of sampling catheter 62 to ambient contaminations only after distal end 76 of insertion sheath 72 has been rotated toward a preselected lung and has been advanced beyond the point 20 at the first bifurcation of trachea 16. At this location in the respiratory system of patient 10 the chances that microorganisms inhabiting the upper respiratory system will attach to outer surface 112 of sampling catheter 62 are substantially reduced. This contributes to more accuracy in the sampling recovered through sampling catheter 62.

According to another aspect of the present invention, sampling catheter 62 comprises a second closure means located at distal end 70 thereof for facilitating wedging of distal end 70 of sampling catheter 62 into a bronchiole of patient 10. As also shown, by way of example and not limitation, in FIGS. 4–6 tip 74 of sampling catheter 62 is provided with a lead surface 118 comprising a smoothly curved dome terminating at outer lateral periphery 110 of tip 74. Aperture 108 is centrally formed in the dome of lead surface 118 so as to communicate with lumen 106 at the interior of sampling catheter 62.

During the advancement of sampling catheter 62 out of insertion sheath 72 and into the preselected one of lungs 22, 24, the size of the air passage through which tip 74 is advanced gradually decreases until lead surface 118 of tip 74 wedges within the walls of a single bronchiole. The shape of lead surface 118 assists in the process of initial wedging by continuing to deflect tip 74 away from the wall of the air passageway into which sampling catheter 62 is being advanced, until the walls of that air passageway uniformly surround and close upon the circumference of tip 72 at outer lateral periphery 110 thereof. The smooth shape of lead surface 118 has the effect of minimizing trauma as wedging is actually affected.

Thereafter, the mushroom-shaped cross-section of tip 74, and in particular, the overhang at outer lateral periphery 110 thereof, prevents the inadvertent withdrawal of tip 74 from its wedged position. Tissue from the wall of the air passageway in which tip 74 is wedged, presses about the full circumference of outer lateral periphery 110. The tissue of the air passageway walls on the same side of outer lateral periphery 110 as proximal surface 114 becomes disposed radially inwardly of outer lateral periphery 110 behind head portion 102 of tip 74. This tissue tends desirably to hold head portion 102 in its wedging position, and the infusion and aspiration of sampling fluid as required for bronchoalveolar lavage can thereafter be safely and reliably undertaken.

The steps for utilizing bronchoalveolar lavage catheter 60 will be reviewed with reference to the series of FIGS. 7A through 7D. Insertion sheath 72 with sampling catheter 62 disposed therein in the manner shown in FIG. 2 is introduced into endotracheal tube 12 through an appropriate coupling, such as elbow coupling 42 and bronchoalveolar lavage catheter access port 44. The assembly of insertion sheath 74 with sampling catheter 62 therein is advanced through the upper respiratory system of patient 10 and to distal end 18 of endotracheal tube 12. This is the position of distal end 76 of insertion sheath 72 shown in solid lines in FIG. 7A.

Thereafter, the assembly of insertion sheath 72 with sampling catheter 62 therein is advanced out of distal end 18 of endotracheal tube 12 into trachea 16 of the upper respiratory system of patient 10. The advancement of the assembly is terminated above point 20 at the first bifurcation of trachea 16. This is the position of insertion sheath 72 shown in dashed lines in FIG. 7A. As thus shown, the bend at distal end 76 of insertion sheath 72 is oriented toward right mainstem bronchus 24 leading into right lung 22 (not shown). Were sampling catheter 62 to be advanced out of distal end 76 of insertion sheath 72 with distal end 76 of insertion sheath 72 disposed in the orientation illustrated in dashed lines in FIG. 7A, then tip 74 of sampling catheter 62 would advance into right mainstem bronchus 24 and ultimately into right lung 22 (not shown) of patient 10. Nevertheless, due to the structure of insertion sheath 72 in particular, it is possible in the alternative with a high degree of reliability to reorient tip 74 of sampling catheter 62 into left mainstem bronchus 28, so that tip 74 ultimately wedges into a bronchiole in left lung 26 (not shown) of patient 10.

To accomplish this end, it is only necessary to rotate proximal end 80 (FIGS. 2 and 3) of insertion sheath 74 outside the body of patient 10 by an appropriate degree. Because of the relative structural rigidity imparted to insertion sheath 72 by the material of which it is comprised, rotation of proximal end 80 thereof results in a one-to-one rotation of distal end 76 as, for example, illustrated in FIG. 7A by arrow R.

Figure 7A:
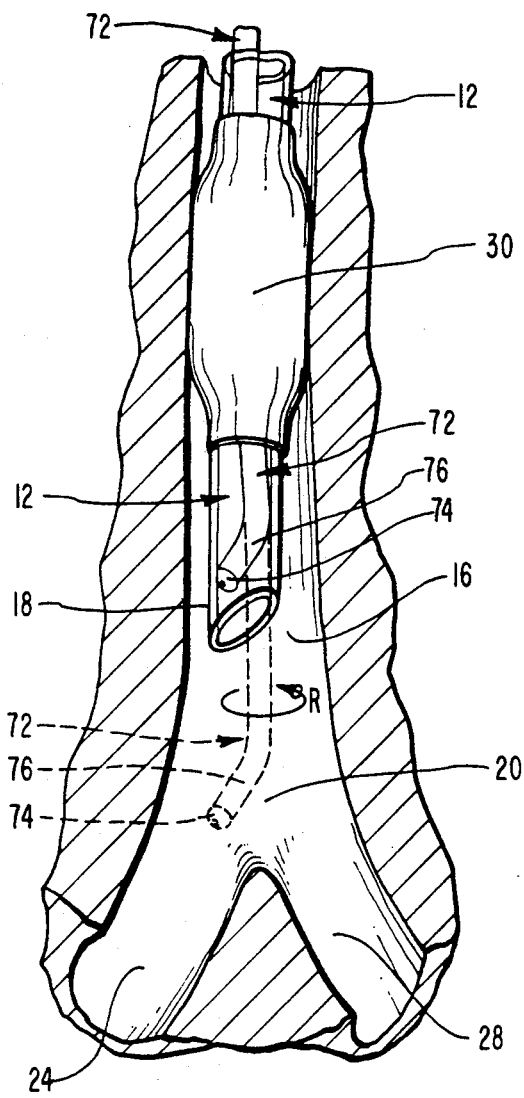
FIGS. 7A through 7D are a sequence of schematic illustrations of a method for inserting and directing the inner catheter of the bronchoalveolar lavage catheter of FIG. 2 into a preselected lung of the patient and wedging the distal tip of the inner catheter in a bronchiole in that lung.
Figure 7B:
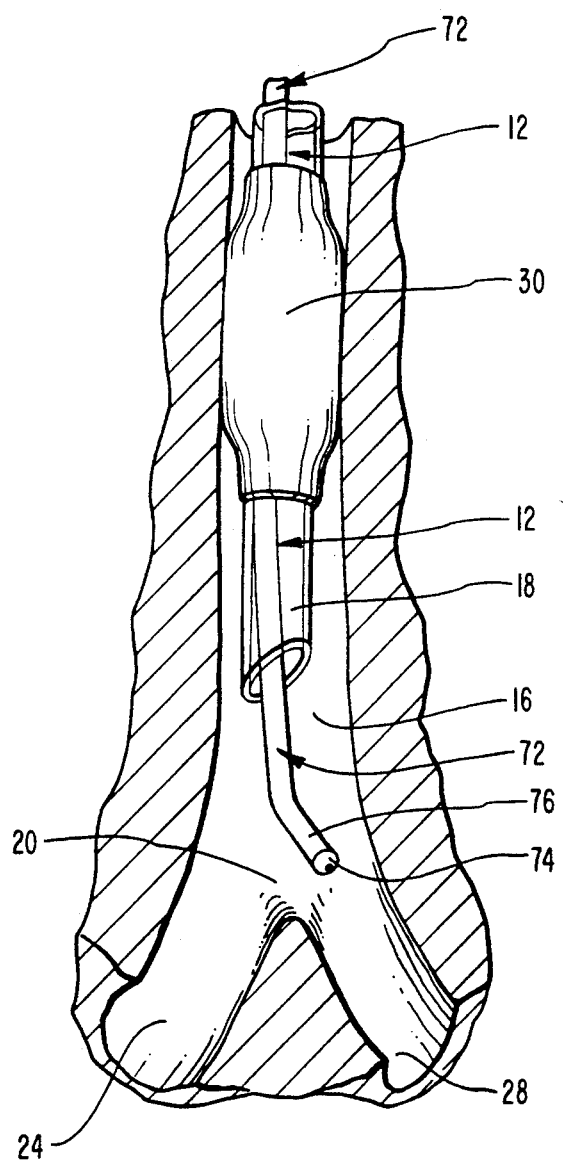
Figure 7C:
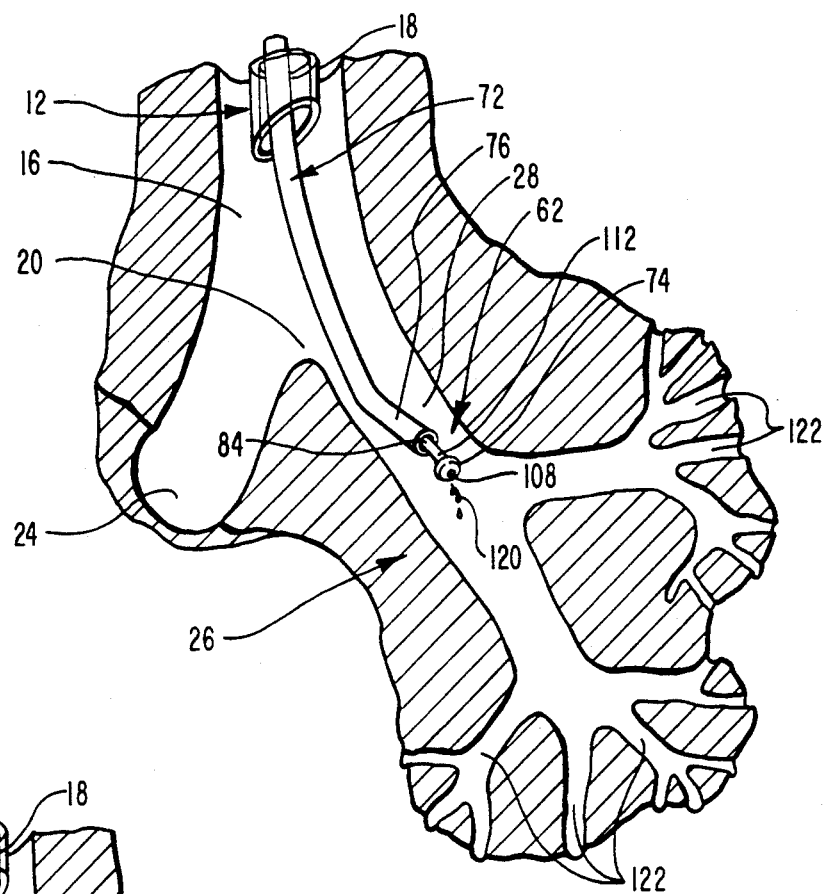

The rotation of insertion sheath 72 about the longitudinal axis thereof in the manner illustrated by arrow R in FIG. 7A will eventually bring the bend at distal end 76 of insertion sheath 72 to be oriented toward left mainstem bronchus 28, as shown in FIG. 7B. In the orientation of distal end 76 of insertion sheath 72 illustrated, the advancement of sampling catheter 62 out of distal end 76 of insertion sheath 72 will direct tip 74 of sampling catheter 62 into left mainstem bronchus 28. Nevertheless, in order to insure this result, it is advisable to further advance the assembly of insertion sheath 72 with sampling catheter 62 somewhat further into the respiratory system of patient 10. In this manner distal end 76 of insertion sheath 72 actually enters left mainstem bronchus 28, assuming for example the position illustrated in FIG. 7C. Then sampling catheter 62 is advanced out of distal end 76 of insertion sheath 72.

Until this has occurred, tip 74 effects a sealing engagement with distal end 76 of insertion sheath 72, and the outer surface 112 of sampling catheter 62 is protected from contamination from the upper respiratory system of patient 10. Nevertheless, the outer surface of tip 74 of sampling catheter 62 can still become contaminated, and aperture 108 centrally formed therein can become blocked with contaminated mucous. Accordingly, after full advancement of insertion sheath 72 into the body of patient 10, distal end 84 of sampling catheter 62 is advanced out of distal end 76 of insertion sheath 72 a short distance and a small quantity of fluid 120 from reservoir 46 (FIG. 1) is used to flush any plug of contaminated mucous from aperture 108 in tip 74. Fluid 120 passes harmlessly into the bronchioles 122 of patient 10 below tip 74.

Figure 7D:
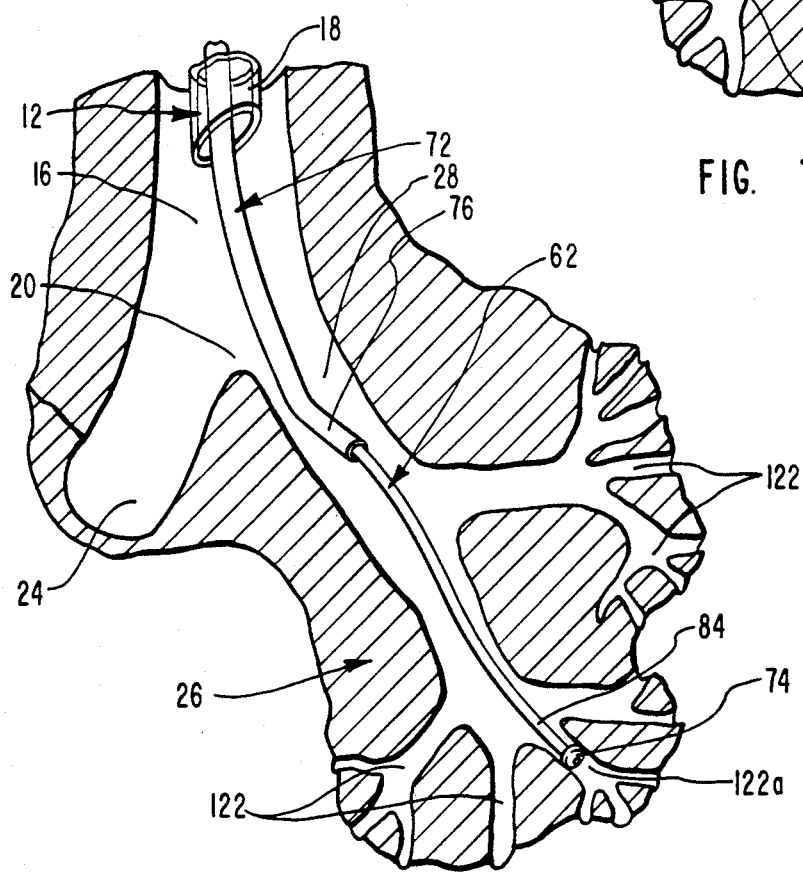

Thereafter, sampling catheter 62 is advanced out of insertion sheath 72 into the bronchioles 122 of patient 10 until tip 74 of sampling catheter 62 becomes wedged in a bronchiole, shown, for example, as bronchiole 122a in FIG. 7D. Wedging may be verified through the appropriate use of air passageway pressure monitor 50. Longitudinal movement of sampling catheter 62 thereafter is advisedly restrained by suitable means, such as those locatable in bronchoalveolar lavage catheter access port 44 (FIG. 1). Thereafter, fluid from reservoir 46 is infused into the position of left lung 26 isolated by the wedging of tip 74 into bronchiole 122a and aspirated using sampling stopcock 66 in combination with syringe 48.

Figure 8:
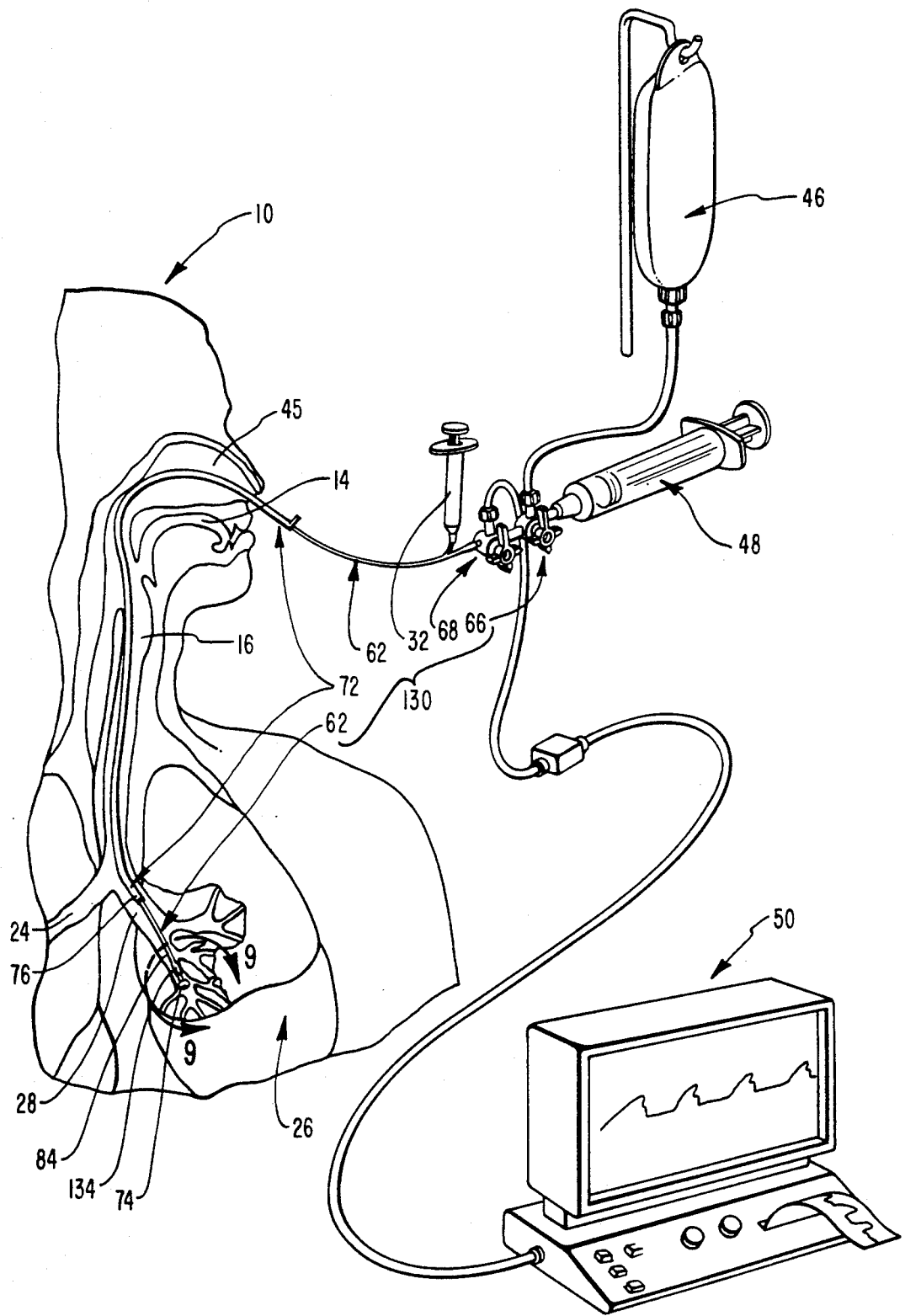
FIG. 8 is a schematic illustration of a system for conducting bronchoalveolar lavage using a second embodiment of an inventive bronchoalveolar lavage catheter.

FIG. 8 illustrates a system for conducting bronchoalveolar lavage using a second embodiment of a bronchoalveolar lavage catheter 130. Structures of bronchoalveolar lavage catheter 130 and the system employed therewith that are identical to corresponding structures associated with bronchoalveolar lavage catheter 60 or the system employed therewith will be referred to by identical reference figures. Accordingly, only the differences between these two embodiments of a bronchoalveolar lavage catheter will be discussed in detail.

In FIG. 8, bronchoalveolar lavage catheter 130 is shown entered into left lung 26 of patient 10 by way of nasal passages 45 and trachea 16 in the upper respiratory system thereof. While the process of conducing bronchoalveolar lavage catheter could, as illustrated in FIG. 1, be conducted through an endotracheal tube, thereby permitting patient 10 to be mechanically ventilated, in FIG. 8 bronchoalveolar lavage catheter 130 is employed without any additional medical equipment. Bronchoalveolar lavage catheter 130 comprises a sampling catheter 62 with a tip 74 at distal end 84 thereof housed and slidable within an insertion sheath 72 having a bend at the distal end 76 thereof that departs at a predetermined bend angle from the longitudinal axis. The proximal end 74 of sampling catheter 62 is coupled through a pressure stopcock 68 to a sampling stopcock 66, both of which perform functions substantially similar to those already described in relation to bronchoalveolar lavage catheter 60 of FIG. 1.

Figure 9:
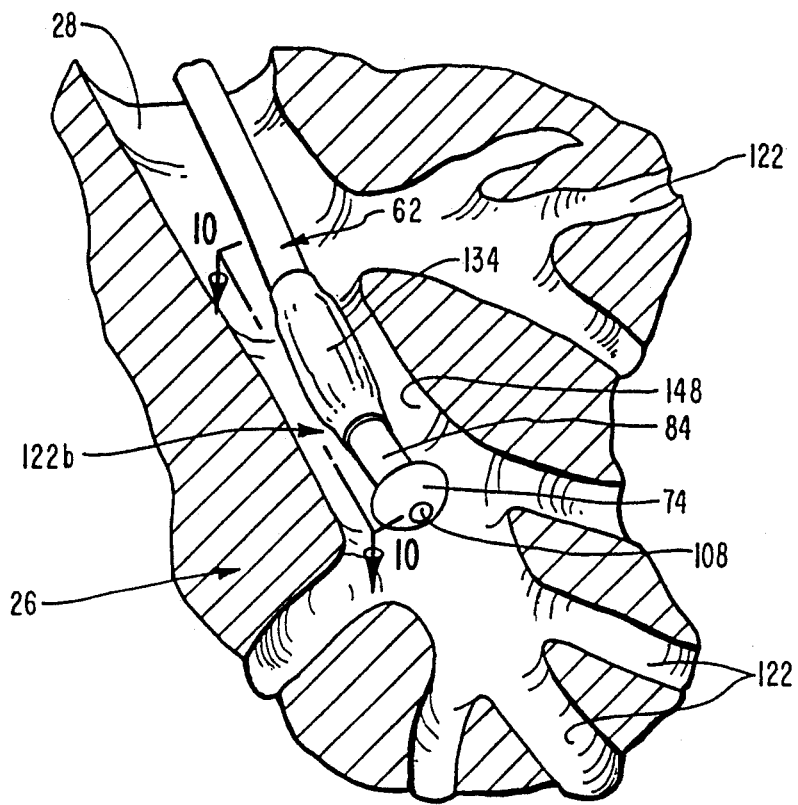
FIG. 9 is a detailed perspective view of the tip of the inner catheter illustrated in FIG. 8.

In contrast therewith, however, bronchoalveolar lavage catheter 130 comprises a balloon inflation syringe 132 and, correspondingly, a flexible cuff 134 shown in additional detail in FIG. 9 as being attached to and encircling outer surface 112 of sampling catheter 62 proximal of tip 74 at distal end 84 thereof.

Figure 10:
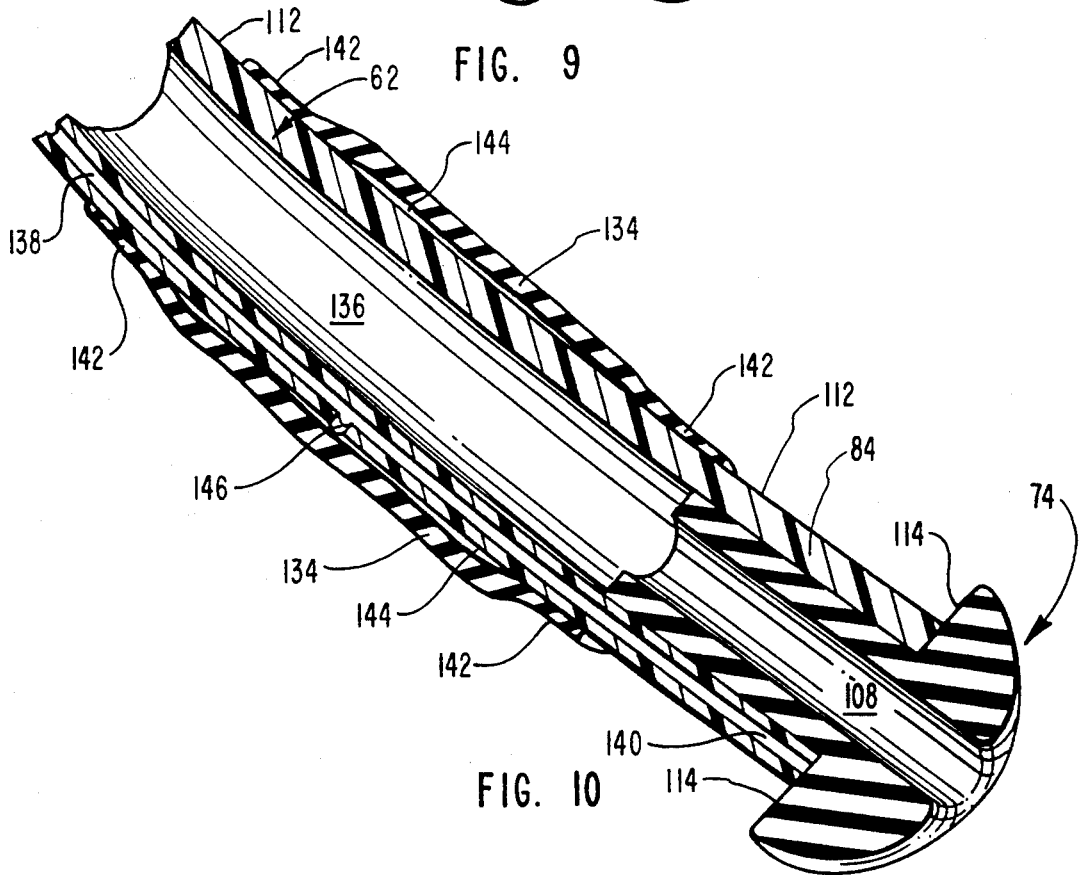
FIG. 10 is a cross-sectional view of the tip of the bronchoalveolar lavage catheter illustrated in FIG. 8 taken along section lines 10—10 shown therein.

As more clearly understood by reference to the cross-section of FIG. 10, sampling catheter 62 of bronchoalveolar lavage catheter 130 comprises a first lumen 136 so sized as to permit the infusion and aspiration of a fluid from reservoir 46 through sampling catheter 62. In addition, however, sampling catheter 62 comprises a second lumen 138 having a size relatively smaller than that of first lumen 136 and being capable of transmitting a gas between balloon inflation syringe 132 and proximal end 64 of sampling catheter 62. Tip 74 of sampling catheter 62 is secured in the end of first lumen 136 in such a manner that proximal surface 114 of tip 74 closes distal end 140 of second lumen 138. Flexible cuff 134 is a generally cylindrical sheet secured at each periphery 142 thereof to outer surface 112 of sampling catheter 62. This defines between flexible cuff 134 and outer surface 112 an annular inflation space 144. An inflation aperture 146 communicates between second lumen 138 and inflation space 144.

Figure 11:
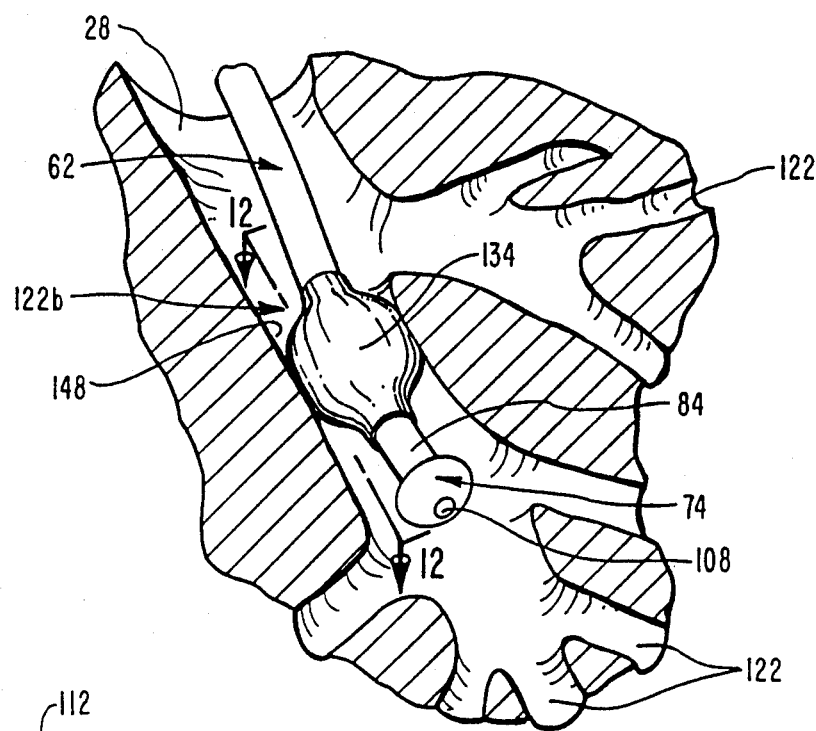
FIG. 11 is a perspective view of the tip of the bronchoalveolar lavage catheter shown in FIG. 9 with the cuff on an exterior surface thereof inflated to engage the walls of the bronchi of the patient.
Figure 12:
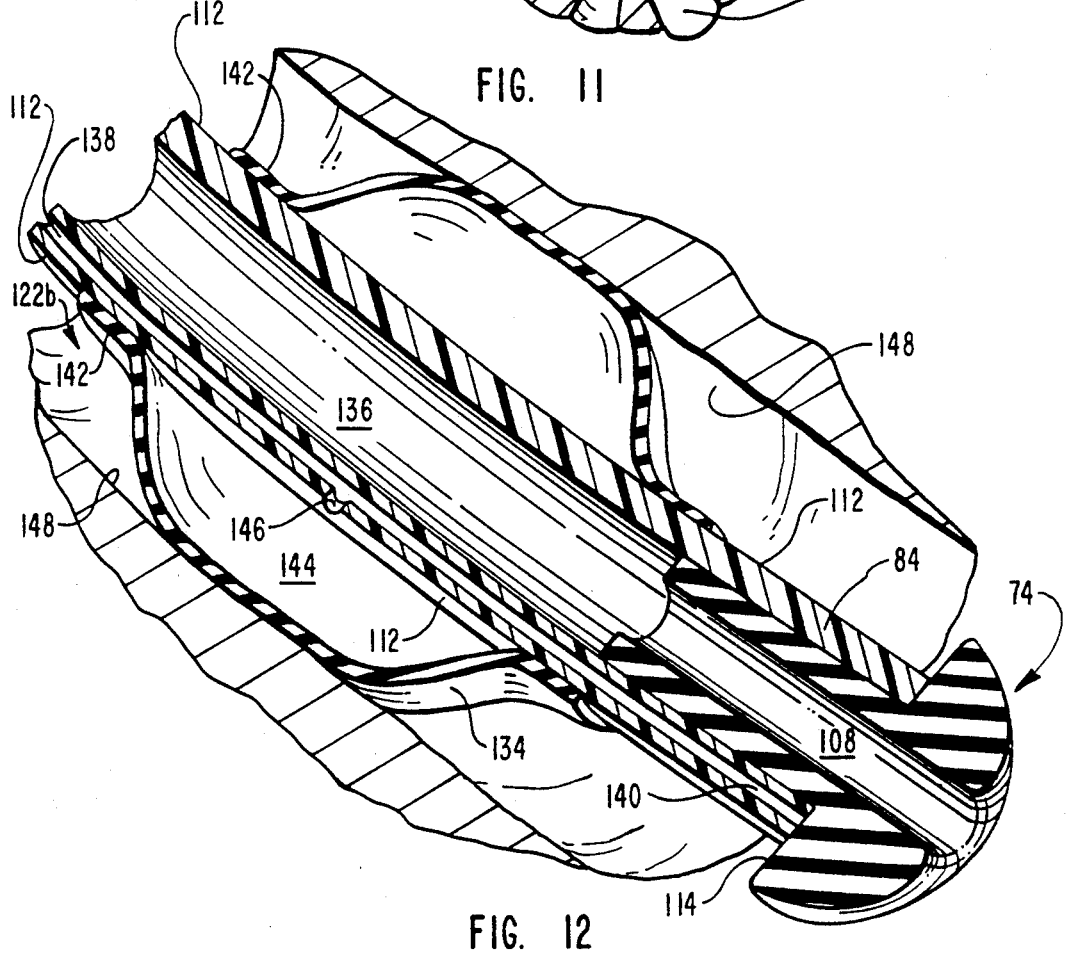
FIG. 12 is a cross-section view of the tip of the second embodiment of a bronchoalveolar lavage catheter shown in FIG. 11 taken along section line 12—12 shown therein.

Flexible cuff 134 is thus inflatable utilizing balloon inflation syringe 132 to force a gas through second lumen 138 and inflation aperture 146 into inflation space 144. The result as illustrated in FIGS. 11 and 12 is the inflation of flexible cuff 134 into engagement with the walls 148 of a bronchiole 122b of patient 10 which is larger in diameter than bronchiole 122a (FIG. 7D) in which tip 74 of sampling catheter 62 could become. Under such conditions, a larger section of a preselected one of lungs 22, 26 of patient 10 can be subjected to bronchoalveolar lavage sampling.

The presence of flexible cuff 134 on outer surface 112 of sampling catheter 62 affects the relative sizing in sampling catheter 62 and in insertion sheath 74. Without any inflation cuff such as flexible cuff 134, insertion sheath 72 might typically be a sixteen French catheter and sampling catheter 62 a twelve French catheter. Additional clearance between these two structures is required, however, if sampling catheter 62 with flexible cuff 134 secured to the exterior thereof is to be moveable freely and longitudinally within insertion sheath 72. Accordingly, if insertion sheath 72 is a sixteen French catheter, sampling catheter 62 should be reduced in size to that of a ten French catheter. Alternatively, if sampling catheter 62 is a twelve French catheter, insertion sheath 72 should be increased in size to that of an eighteen French catheter.

The inventive bronchoalveolar lavage catheters disclosed are substantial advances towards improving the accuracy and ease of diagnosing inflammations and other abnormalities of the lungs. The practitioner utilizing the inventive bronchoalveolar lavage catheter can with reliability sample from either the left or the right lung and do so in the manner which minimizes contamination by the upper respiratory system, either of the equipment utilized at the sampling site, or of the lower respiratory system of the patient. The ease of catheter placement facilitated by the inventive bronchoalveolar lavage catheter eliminates the need in conducting bronchoalveolar lavage to resort to costly bronchoscopic techniques. Accordingly, the inventive bronchoalveolar lavage catheter is so inexpensive to produce as to render it disposable. This obviates the need for expensive equipment inventories and costly and time consuming sterilizations between procedures.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Patent is:

1. An assembly for performing bronchoalveolar lavage, said assembly comprising:
   (a) a sampling catheter so sized and configured as to extend from a bronchiole in the lung of a patient through the upper respiratory system of the patient, said sampling catheter comprising proximal and distal ends and further comprising a single lumen means for both infusing and aspirating fluid therethrough, said single lumen means communicating with both said sampling catheter proximal and distal ends;
   (b) means located at the proximal end of said sampling catheter for infusing and aspirating fluid through said single lumen means at said distal end; and
   (c) means for directing the distal end of said sampling catheter into a preselected lung of the patient and for protecting the outside of said sampling catheter from contamination during advancement of said distal end of said sampling catheter through the upper respiratory system of the patient.

2. An assembly as recited in claim 1, wherein said means for directing and for protecting comprises an elongated insertion sheath so sized and configured as to encircle said sampling catheter and to be capable of extending from below the first bifurcation of the trachea of the patient through the upper respiratory system of the patient.

3. An assembly as recited in claim 2, wherein said insertion sheath possess sufficient structural rigidity as to be capable, when disposed in the upper respiratory system of the patient, of exhibiting at the distal end thereof one-to-one rotation about the longitudinal axis thereof relative to the proximal end thereof.

4. An assembly as recited in claim 3, wherein the distal end of said insertion sheath is displaced at a predetermined bend angle to the longitudinal axis of said insertion sheath.

5. An assembly as recited in claim 4, wherein the proximal end of said insertion sheath is provided with a direction indicator designating the radial direction at which said distal end of said insertion sheath departs from the longitudinal axis thereof.

6. An assembly as recited in claim 3, wherein said insertion sheath is comprised of ethyl vinyl acetate.

7. An assembly as recited in claim 2, wherein said sampling catheter comprises a tip at the distal end thereof, the outer lateral periphery of said tip having a diameter larger than the outer surface of said sampling catheter, said tip having a proximal surface between said outer lateral periphery and said outer surface of said sampling catheter capable of sealingly engaging said distal end of said insertion sheath when said insertion sheath is disposed encircling said sampling catheter with said distal end of said sampling catheter at said distal end of said insertion sheath.

8. An assembly as recited in claim 7, wherein said sampling catheter is provided with a position indicator mark at the location on said sampling catheter disposed at said proximal end of said insertion sheath when said tip of said sampling catheter sealingly engages said distal end of said insertion sheath.

9. An assembly as recited in claim 7, wherein the surface of said tip opposite from said proximal surface thereof defines a lead surface of said tip, and wherein said lead surface of said tip comprises a smoothly curving dome terminating at said outer lateral periphery of said tip, thereby to facilitate wedging of said distal end of said sampling catheter into a bronchiole of the patient.

10. An assembly as recited in claim 2, wherein said sampling catheter comprises a tip at the distal end thereof, said tip having a lead surface comprising a smoothly curving dome terminating at the outer lateral periphery of said tip, thereby to facilitate wedging of said distal end of said sampling catheter into a bronchiole of a patient.

11. An assembly as recited in claim 10, wherein said tip has a diameter larger than the outer surface of said sampling catheter, whereby said tip has a proximal surface between said outer lateral periphery and said outer surface of said sampling catheter which sustains wedging of the distal end of said sampling catheter in a bronchiole of a patient.

12. An assembly as recited in claim 11, wherein said tip is comprised of a soft, biocompatible material, thereby to minimize trauma to patient tissue due to wedging of said distal end of said sampling catheter into a bronchiole of the patient.

13. An assembly as recited in claim 11, wherein said outer lateral periphery of said tip has a diameter larger than the diameter of the outer surface of said sampling catheter.

14. An assembly as recited in claim 13, wherein the surface between said outer lateral periphery of said tip and said outer surface of said sampling catheter defines a proximal surface of said tip, and said proximal surface of said tip is capable of sealingly engaging said distal end of said insertion sheath when said insertion sheath is disposed encircling said sampling catheter with said distal end of said sampling catheter at said distal end of said insertion sheath.

15. An assembly as recited in claim 14, wherein said sampling catheter is provided with a position indicator mark at the location on said sampling catheter disposed at said proximal end of said insertion sheath when said tip of said sampling catheter sealingly engages said distal end of said insertion sheath.

16. An assembly as recited in claim 1, wherein said sampling catheter comprises a flexible cuff attached to and encircling the sides of said sampling catheter proximal of said distal end thereof, said cuff being selectively inflatable through said sampling catheter to engage the walls of a bronchiole of the patient.

17. An assembly as recited in claim 1, wherein said means for infusing and for aspirating comprises a sampling stopcock located at said proximal end of said sampling catheter, said sampling stopcock being connectable to a reservoir of a fluid and to a syringe for infusing the fluid through the sampling catheter.

18. An assembly as recited in claim 18, wherein said sampling stopcock is capable of selectively placing the syringe alternately in communication with the reservoir of fluid or with said proximal end of said sampling catheter.

19. A catheter for performing bronchoalveolar lavage, said catheter comprising:
    (a) an outer catheter so sized and configured as to extend from below the first bifurcation of the trachea of a patient through the upper respiratory system of the patient;
    (b) an inner catheter disposable inside said outer catheter and being so sized and configured as to extend from a bronchiole in the lung of a patient through the upper respiratory system of the patient, said inner catheter comprising proximal and distal ends and further comprising a single lumen means for both infusing and aspirating fluid therethrough, said single lumen means communicating with both said inner catheter proximal and distal ends; and
    (c) means located at said proximal end of said inner catheter for infusing and aspirating fluid through said single lumen means at said distal end.

20. A catheter as recited in claim 19, wherein said inner catheter comprises a first closure means located at said distal end of said inner catheter for sealing the distal end of said outer catheter when said outer catheter is disposed encircling said inner catheter with said distal end of said inner catheter at said distal end of said outer catheter.

21. A catheter as recited in claim 20, wherein said first closure means comprises a tip at the distal end of said inner catheter, said tip having an outer lateral periphery larger in diameter than the outer surface of said inner catheter, and said tip having a proximal surface between said outer lateral periphery and said outer surface of said inner catheter capable of sealingly engaging said distal end of said outer catheter when said outer catheter is disposed encircling said inner catheter with said distal end of said inner catheter at said distal end of said outer catheter.

22. A catheter as recited in claim 21, wherein said tip is secured in the opening at said distal end of said inner catheter.

23. A catheter as recited in claim 19, wherein said inner catheter comprises a second closure means for facilitating wedging of said distal end of said inner catheter into a bronchiole of a patient.

24. A catheter as recited in claim 23 wherein said second closure means comprises a tip at said distal end of said inner catheter, the lead surface of said tip comprising a smoothly curving dome terminating at the outer lateral periphery of said tip, said dome having formed centrally therethrough an aperture communicating with the interior of said inner catheter.

25. A catheter as recited in claim 24, wherein said tip is secured in the opening at said distal end of said inner catheter.

26. An assembly as recited in claim 19, wherein said inner catheter comprises a tip at the distal end thereof, the outer lateral periphery of said tip having a diameter larger than the outer surface of said inner catheter, said tip having a proximal surface between said outer lateral periphery and said outer surface of said inner catheter capable of sealingly engaging said distal end of said outer catheter when said outer catheter is disposed encircling said inner catheter with said distal end of said inner catheter at said distal end of said outer catheter.

27. An assembly as recited in claim 26, wherein said inner catheter is provided with a position indicator mark at the location on said inner catheter disposed at said proximal end of said outer catheter when said tip of said inner catheter sealingly engages said distal end of said outer catheter.

28. An assembly as recited in claim 26, wherein the surface of said tip opposite from said proximal surface thereof defines a lead surface of said tip, and wherein said lead surface of said tip comprises a smoothly curving dome terminating at the outer lateral periphery of said tip, thereby to facilitate wedging of said distal end of said inner catheter into a bronchiole of said patient.

29. An assembly as recited in claim 28, wherein said tip has a diameter larger than the outer surface of said inner catheter, whereby said tip has a proximal surface between said outer lateral periphery and said outer surface of said inner catheter which sustains wedging of the distal end of said inner catheter in a bronchiole of a patient.

30. An assembly as recited in claim 19, wherein said inner catheter comprises a tip at the distal end thereof, said tip having a lead surface comprising a smoothly curving dome terminating at the outer lateral periphery of said tip, thereby to facilitate wedging of said distal end of said inner catheter into a bronchiole of a patient.

31. An assembly as recited in claim 30, wherein said tip has a diameter larger than the outer surface of said inner catheter, whereby said tip has a proximal surface between said outer lateral periphery and said outer surface of said inner catheter which sustains wedging of the distal end of said inner catheter in a bronchiole of a patient.

32. An apparatus as recited in claim 30, wherein said tip is comprised of a radio-opaque material.

33. An assembly as recited in claim 19, wherein said inner catheter comprises a tip secured in the opening at the distal end thereof, said tip having a mushroom-shaped transverse cross-section.

34. An assembly as recited in claim 33, wherein the surface between said outer lateral periphery of said tip and said outer surface of said inner catheter defines a proximal surface of said tip, and said proximal surface of said tip is capable of sealingly engaging said distal end of said outer catheter when said outer catheter is disposed encircling said inner catheter with said distal end of said inner catheter at said distal end of said outer catheter.

35. An assembly as recited in claim 34, wherein said inner catheter is provided with a position indicator mark at the location on said inner catheter disposed at said proximal end of said outer catheter when said tip of said inner catheter sealingly engages said distal end of said outer catheter.

36. A catheter as recited in claim 19, wherein said inner catheter comprises a single lumen so sized as to permit the infusion and aspiration of a fluid therethrough.

37. A catheter as recited in claim 19, wherein said inner catheter comprises:
(a) a first lumen so sized as to permit the infusion and aspiration of a fluid through said inner catheter; and
(b) a second lumen having a size relatively smaller than that of said first lumen and being capable of transmitting a gas between said distal and said proximal ends of said inner catheter.

38. A catheter as recited in claim 37, wherein said inner catheter comprises a flexible cuff attached to and encircling the sides of said inner catheter proximal of said distal end thereof, said cuff being selectively inflatable by a gas passed through said second lumen of said inner catheter, thereby to engage the walls of a bronchiole of the patient.

39. A catheter as recited in claim 38, wherein said inner catheter is a ten French catheter.

40. A catheter as recited in claim 39, wherein said outer catheter is a sixteen French catheter.

41. A catheter as recited in claim 39, wherein said outer catheter comprises an eighteen French catheter.

42. A catheter as recited in claim 41, wherein said inner catheter comprises a twelve French catheter.

43. A catheter as recited in claim 19, wherein said inner catheter comprises a flexible cuff attached to and encircling the sides of said inner catheter proximal of said distal end thereof, said cuff being selectively inflatable to engage the walls of a bronchiole of the patient.

44. A catheter as recited in claim 19, wherein said inner catheter is comprised of polyvinylchloride.

45. A catheter as recited in claim 44, wherein said outer catheter is a sixteen French catheter.

46. A catheter as recited in claim 19, wherein said inner catheter comprises a twelve French catheter.

47. A catheter as recited in claim 19, wherein said outer catheter possess sufficient structural rigidity as to be capable, when disposed in the upper respiratory system of the patient, of exhibiting at the distal end thereof one-to-one rotation about the longitudinal axis thereof relative to the proximal end thereof.

48. A catheter as recited in claim 47, wherein the distal end of said outer catheter is displaced at a predetermined bend angle to the longitudinal axis of said outer catheter.

49. A catheter as recited in claim 48, wherein the proximal end of said outer catheter is provided with a direction indicator designating the direction at which said bend at said distal end of said outer catheter departs from the longitudinal axis thereof.

50. A catheter as recited in claim 47, wherein said outer catheter is comprised of ethyl vinyl acetate.

51. A catheter as recited in claim 19, wherein said means for infusing and for aspirating comprises a sampling stopcock located at said proximal end of said sampling catheter, said sampling stopcock being connectable to a reservoir of a fluid and to a syringe for infusing the fluid through the inner catheter.

52. A catheter as recited in claim 51, wherein said sampling stopcock is capable of selectively placing the syringe alternately in communication with the reservoir of fluid or with said proximal end of said outer catheter.

53. A catheter as recited in claim 19, further comprising means for monitoring pressure in the airways of the patient.

54. A catheter as recited in claim 53, wherein said means for monitoring pressure comprises a pressure stopcock located between said proximal end of said inner catheter and said means for infusing and aspirating.

55. A catheter as recited in claim 54, wherein said pressure stopcock is capable of selectively placing said proximal end of said inner catheter in communication alternatively with a pressure monitor or with said means for infusing and aspirating.

56. A catheter for performing nonbronchoscopic bronchoalveolar lavage, said catheter comprising:
(a) an elongated insertion sheath so sized and configured as to extend from below the first bifurcation of the trachea of the patient through the upper respiratory system of the patient, said insertion sheath possessing sufficient rigidity as to be capable, when disposed in the upper respiratory system of a patient, of exhibiting at the distal end thereof one-to-one rotation about the longitudinal axis thereof relative to the proximal end thereof, said distal end of said insertion sheath being displaced at a predetermined bend angle to the longitudinal axis thereof;

(b) a sampling catheter disposable inside said outer catheter and being so sized and configured as to extend from a bronchiole of the lung of a patient through the upper respiratory system of the patient, said sampling catheter comprising proximal and distal ends and further comprising at least a single lumen for both infusing and aspirating fluids therethrough in communication with both said sampling catheter proximal and distal ends;

(c) a closure tip secured in said distal end of said sampling catheter, said closure tip comprising:
  (i) an outer lateral periphery larger in diameter than the diameter of the outer surface of said sampling catheter;
  (ii) a proximal surface between said outer lateral periphery thereof and said outer surface of said sampling catheter capable of sealingly engaging said distal end of said insertion sheath when said insertion sheath is disposed encircling said sampling catheter with said distal end of said sampling catheter at said distal end of said insertion sheath;
  (iii) a lead surface at the opposite end of said closure tip from said proximal surface comprising a smoothly curving dome terminating at said outer lateral periphery of said closure tip, thereby facilitating wedging of said distal end of said sampling catheter into a bronchiole of the patient; and
  (iv) an aperture centrally formed through said closure tip from said dome to the interior of said sampling catheter; and (d) a sampling stopcock located at the proximal end of said sampling catheter and connectable to a reservoir of a fluid and to a syringe for infusing the fluid through the sampling stopcock being capable of selectively placing the syringe alternately in communication with the reservoir of fluid or said proximal end of said sampling catheter, said communication being through said sampling catheter single lumen.

57. A catheter as recited in claim 56, further comprising a pressure stopcock located between said proximal end of said sampling catheter and said sampling stopcock, said stopcock being capable of selectively placing said proximal end of said sampling catheter in communication alternatively with a pressure monitor or with said sampling stopcock.

58. A catheter as recited in claim 56, wherein said sampling catheter comprises a single lumen so sized as to permit the infusion and aspiration of a fluid therethrough.

59. A catheter as recited in claim 56, wherein said sampling catheter comprises:
  (a) a first lumen so sized as to permit the infusion and aspiration of a fluid through said sampling catheter; and
  (b) a second lumen having a size relatively smaller than that of said first lumen and being capable of transmitting a gas between said distal end said proximal ends of said sampling catheter.

60. A catheter as recited in claim 59, further comprising a flexible cuff attached to and encircling the sides of said sampling catheter proximal of said distal end thereof, said cuff being inflatable by a gas passed through said second lumen of said sampling catheter, thereby to engage the walls of a bronchiole of the patient.

61. A method for performing bronchoalveolar lavage, said method comprising the steps:
  (a) the securing in the distal end of a sampling catheter a closure tip comprising:
    (i) an outer lateral periphery larger in diameter than the diameter of the outer surface of said sampling catheter;
    (ii) a proximal surface between said outer later periphery thereof and said outer surface of said sampling catheter, said sampling catheter having proximal and distal ends and further having therethrough at least a single lumen in communication with both said sampling catheter proximal and distal ends;
    (iii) a lead surface at the opposite end of said closure tip from said proximal surface comprising a smoothly curving dome terminating at said outer lateral periphery of said closure tip; and
    (iv) an aperture centrally formed through said closure tip from said dome said aperture communicating with said single lumen of said sampling catheter; and
  (b) disposing said sampling catheter within an elongated insertion sheath so sized and configured as to extend from below the bifurcation of the trachea of the patient through the upper respiratory system, said insertion sheath possessing sufficient rigidity to be capable, when disposed in the upper respiratory system of a patient, of exhibiting at the distal end thereof one-to-one rotation about the longitudinal axis thereof relative to the proximal end thereof, said distal of said insertion sheath being displaced at a predetermined bend angle to the longitudinal axis thereof;
  (c) sealing the distal end of said insertion sheath with said proximal surface of said tip;
  (d) advancing said insertion sheath with said sampling catheter disposed therein through the upper respiratory system of the patient to a point above and proximate to the first bifurcation of the trachea;
  (e) rotating said proximal end of said insertion sheath, whereby said distal end thereof become oriented at said predetermined bend angle towards a preselected branch of the trachea;
  (f) advancing said insertion sheath with said sampling catheter disposed therein into said preselected branch of the trachea;
  (g) advancing said sampling catheter out of said insertion sheath into said preselected branch of the trachea;
  (h) flushing from said aperture of said closure tip contaminates from the upper respiratory system of the patient;
  (i) wedging said closure tip in a bronchiole; and
  (j) infusing and withdrawing a solution through said single lumen at said distal end into the portion of the lung communicating with the bronchiole in which said closure tip is wedged.

* * * * *

UNITED STATES PATENT AND TRADEMARK OFFICE
CERTIFICATE OF CORRECTION

PATENT NO. : 5,165,420
DATED : November 24, 1992
INVENTOR(S) : RICHARD D. STRICKLAND It is certified that error appears in the above-identified patent and that said Letters Patent is hereby corrected as shown below:

Title page, column 2, line 8 of Abstract, "laterial" should be --lateral--
    Column 3, line 65, after "catheter" insert --.--
    Column 6, line 42, "cross-section view" should be --cross-sectional view--
    Column 9, line 46, after "FIG. 3" insert --.--
    Column 12, line 53, "conducing" should be --conducting--
    Column 14, line 44, "possess" should be --possesses--
    Column 15, line 67, "as recited in claim 18," should be --as recited in claim 17,--
    Column 17, line 33, "radio-opaque" should be --radiopaque--
    Column 18, line 25, "possess" should be --possesses--
    Column 19, lines 10-11, "outer catheter" should be --elongated insertion sheath--
    Column 19, line 21, "()i)" should be --(i)--
    Column 20, line 41, after "distal" insert --end--

Signed and Sealed this

Thirtieth Day of November, 1993

Attest:

BRUCE LEHMAN

Attesting Officer      Commissioner of Patents and Trademarks